(12) United States Patent
Hamamoto et al.

(10) Patent No.: US 8,697,096 B2
(45) Date of Patent: Apr. 15, 2014

(54) TAPE PREPARATION COMPRISING ETODOLAC IN IONIC LIQUID FORM

(75) Inventors: Hidetoshi Hamamoto, Higashikagawa (JP); Yasushi Miwa, Higashikagawa (JP)

(73) Assignee: MEDRx Co., Ltd., Kagawa (JP)

( * ) Notice: Subject to any disclaimer, the term of this patent is extended or adjusted under 35 U.S.C. 154(b) by 127 days.

(21) Appl. No.: 12/746,632

(22) PCT Filed: Dec. 9, 2008

(86) PCT No.: PCT/JP2008/003659
§ 371 (c)(1),
(2), (4) Date: Jun. 7, 2010

(87) PCT Pub. No.: WO2009/075094
PCT Pub. Date: Jun. 18, 2009

(65) Prior Publication Data
US 2010/0280090 A1    Nov. 4, 2010

(30) Foreign Application Priority Data

Dec. 11, 2007 (JP) ................................. 2007-320125

(51) Int. Cl.
*A61K 9/00* (2006.01)

(52) U.S. Cl.
USPC ....................................................... 424/400

(58) Field of Classification Search
USPC ....................................................... 424/400
See application file for complete search history.

(56) References Cited

U.S. PATENT DOCUMENTS

| | | | |
|---|---|---|---|
| 4,164,563 A * | 8/1979 | Chang | 514/18.8 |
| 5,695,779 A * | 12/1997 | Mori | 424/448 |
| 7,378,108 B1 * | 5/2008 | Iga et al. | 424/443 |
| 2003/0125308 A1 * | 7/2003 | Inamoto et al. | 514/165 |
| 2007/0026025 A1 * | 2/2007 | Mitchell | 424/400 |
| 2007/0054952 A1 | 3/2007 | Hamamoto et al. | |
| 2009/0264664 A1 | 10/2009 | Endo et al. | |

FOREIGN PATENT DOCUMENTS

| | | | |
|---|---|---|---|
| JP | 64-40420 | | 2/1989 |
| JP | 2002-128699 | | 5/2002 |
| JP | 2005-82512 | | 3/2005 |
| JP | 2005-239709 | | 9/2005 |
| WO | WO 0048634 | * | 8/2000 |
| WO | 2007/046544 | | 4/2007 |

OTHER PUBLICATIONS

Machine translation of JP 2005-239709.*
Kuraray (Septon product information Nov. 3, 2004).*
International Search Report issued Jan. 27, 2009 in International (PCT) Application No. PCT/JP2008/003659.
English translation of the International Preliminary Report on Patentability and Written Opinion.

* cited by examiner

*Primary Examiner* — David J Blanchard
*Assistant Examiner* — Devang Thakor
(74) *Attorney, Agent, or Firm* — Wenderoth, Lind & Ponack, L.L.P.

(57) ABSTRACT

Disclosed is a tape preparation comprising etodolac in an ionic liquid form, which has high transdermal absorbability. Etodolac is reacted with an organic amine compound to produce an ionic liquid of etodolac. By using the ionic liquid, it becomes possible to increase the transdermal absorbability of etodolac. Further for the purpose of enhancing the transdermal absorbability and the tissue penetration ability of an ionic solution of etodolac, the composition of an organic solvent system for the ionic solution of etodolac is investigated, and it is found that a mixed solvent of an alcohol and an ester (1:2 to 2:1) is suitable as the organic solvent. Still further, an appropriate adhesion force can be achieved by properly selecting a softening agent. In this manner, a tape preparation having good transdermal absorbability can be prepared. The tape preparation can exert its pharmacological efficacy rapidly, and is therefore extremely effective for the teatment of a chronic pain such as rheumatoid arthritis, osteoarthritis and lumbago, an inflammatory diseases such as shoulder periarthritis and tendovaginitis, cervical syndrome, a pain induced by a surgery or an injury, or the like.

8 Claims, 5 Drawing Sheets

US 8,697,096 B2

TAPE PREPARATION COMPRISING ETODOLAC IN IONIC LIQUID FORM

This application is a U.S. national stage of International Application No. PCT/W2008/003659 filed Dec. 9, 2008.

TECHNICAL FIELD

The present invention relates to a tape preparation comprising etodolac in an ionic liquid form having anti-inflammatory and analgesic effects.

BACKGROUND ART

In the past, a Non-Steroidal Anti-Inflammatory Drug (hereinafter referred to as NSAID) has been known as an anti-inflammatory analgesic. The NSAID has an activity to control a production of prostaglandin relating to inflammatory and/or pain generation by inhibiting cyclooxygenase (hereinafter referred to as COX), which catalyzes the first reaction in the arachidonate cascade, a metabolic pathway to potentiate a pain.

However, serious side effects are sometimes reported when the production of prostaglandin is excessively controlled by administration of NSAID since prostaglandin has various effects other than inflammation or pain generation. For example, when COX activity is inhibited, a lipoxygenase activity is stimulated instead and increase of leukotriene reduces gastric secretion; simultaneously mucosa membrane of the digestive organ is damaged by increased active oxygen and ulcer is generated. Examples of other side effects include renal dysfunction, hepatic dysfunction, skin rush and the like, and especially induction of aspirin asthma is fatal among them.

Under this circumstance, a lot of efforts have been poured into developing external preparation of NSAID having less side effects. It would be possible to reduce systemic side effects and realize high drug level at an affected site by transdermal delivery of NSAID thereto.

Some NSAID, however, have quite limited transdermal permeability and the pharmaceutical effect when administered as an external formulation is dramatically reduced compared with those of an oral administration. In response, a composition of external anti-inflammatory analgesic comprising NSAID and a local anesthetic is proposed in order to improve the transdermal absorbability of NSAID (Patent Literature 1).

Patent Literature 2 also discloses a formulation comprising etodolac as NSAID and describes that the transdermal permeability of etodolac is improved when lidocaine is combined with etodolac. But, all that described therein is a broad range of incorporated lidocaine, which is 0.1 to 1.8 molar compared to 1 molar of etodolac, and effect of 1.2 molar of lidocaine combined with 1 molar of etodolac in test example 1. Characteristic transdermal permeability and/or tissue penetration ability of the present invention, which is a tape preparation comprising an ionic liquid of etodolac (ambient temperature molten salt with equimolar lidocaine), is therefore never disclosed.

Further Patent Literature 3 describes that a formation of ionic liquid enhances transdermal permeability of an agent, but it is not disclosed whether a usual formulation technique is applicable or not when an ionic liquid of the agent is formed, much less the appropriate formulation recipe was predicted regarding an ionic liquid of etodolac, Patent Literature 1: JP2002-128699A
Patent Literature 2: JP2005-239709A
Patent Literature 1: JP2005-82512A

DISCLOSURE OF INVENTION

Problems to be Solved by the Invention

A problem to be solved in the present invention is to provide with a tape preparation comprising an ionic liquid of etodolac having an excellent transdermal permeability as well as property to demonstrate an anti-inflammatory analgesic effect soon after being applied to skin.

Means for Solving the Problems

The present inventors have extensively studied a tape preparation as a new formulation for an ionic liquid of etodolac. Consequently, they found that a remarkable effect of transdermal absorption as well as an excellent tissue penetration were obtained when an ionic liquid was formed with lidocaine or triisopropanol amine as an organic amino compound and a mixed solvent of an alcohol and an ester as an organic solvent was suitably selected. Moreover they found how to adjust adhesibility of the tape preparation by selecting of a softener and finally achieved the present invention.

Summary of the present invention is as follows;
(1) a tape preparation comprising an ionic liquid of etodolac, characterized in that
  a) etodolac forms an equimolar salt with lidocaine or triisopropanol amine,
  b) an organic solvent, in which alcohol and ester are mixed with ratio of 1:2 to 2:1, is added and
  c) a gelled hydrocarbon is included as a softener.
(2) the tape preparation according to (1) above, wherein the ionic liquid of etodolac is a salt of etodolac with lidocaine,
(3) the tape preparation according to (1) or (2) above, wherein the alcohol is propylene glycol,
(4) the tape preparation according to any of (1) to (3) above, wherein the ester is diethyl sebacate,
(5) the tape preparation according to any of (1) to (4) above, wherein vaseline is added further as a softener,
(6) the tape preparation according to any of (1) to (5) above, wherein the gelled hydrocarbon is plastibase,
(7) the tape preparation according to any of (1) to (6) above, wherein 1 to 5 (w/w) % of etodolac is included,
(8) the tape preparation according to any of (1) to (7) above, wherein the alcohol and the ester are added with the same composition ratio (w/w %),
(9) the tape preparation according to any of (1) to (8) above, wherein a tackifier resin is one or more selected from polybutene, hydrogenated petroleum resin, and a terpene resin,
(10) the tape preparation according to any of (1) to (9) above, wherein the tackifier resin is a terpene resin,

EFFECT OF THE INVENTION

A tape preparation comprising an ionic liquid of etodolac in the present invention has an excellent transdermal permeability and tissue penetration ability, rapidly exerts its pharmaceutical activity and also has a good adhesive property. Therefore, the preparation is effective for the treatment of chronic pain such as rheumatoid arthritis, osteoarthritis, and lumbago, an inflammatory disease such as shoulder periarthritis and tendovaginitis, cervical syndrome, a pain induced by a surgery or an injury or the like.

BEST MODE FOR CARRYING OUT THE INVENTION

Examples of "alcohols" in the present application include a higher alcohol such as benzyl alcohol, lauryl alcohol, myristyl alcohol, cetyl alcohol, stearyl alcohol, cetearyl alcohol, 2-octyldodecanol and the like, a C1-C10 lower alcohol such as ethanol, propanol, isopropanol, n-butanol, pentanol, octanol, dodecanol and the like, or a multivalent alcohol such as ethylene glycol, propylene glycol, 1,3-butylene glycol, polyethylene glycol and the like. Among them, ethanol, isopropanol, ethylene glycol and propylene glycol are preferable.

Examples of "esters" in the present application include ketones such as methyl isobutyl ketone; lower alkyl carboxylic acid esters such as ethyl acetate, propyl acetate, ethyl butylate and the like; fatty acid esters such as diethyl sebacate, isopropyl myristate, diisopropyl adipate, myristyl palmitate, stearyl stearate, myristyl myristate, oleic acid triglyceride, seryl lignocerate, lacceryl serolate, lacceryl laccerylate, carbonate such as propylene carbonate and vegetable oils such as olive oil, palm oil and the like. Among them, fatty acid esters such as isopropyl myristate, diethyl sebacate and the like and vegetable oils such as palm oil, olive oil and the like are preferable.

A wording of "addition of an organic solvent with the composition ratio of 1:2 to 2:1(w/w %)" means that the alcohols and the esters above are mixed in the range of the composition rate of 1:2 to 2:1 (w/w %) and used as a solvent. Preferably the range of the composition rate of 1:1.5 to 1.5:1 (w/w %) is exemplified and the composition ratio of about 1:1 is more preferable.

In addition, transdermal absorbability tends to be reduced beyond the range of the above composition ratio (1:2 to 2:1). For example, the transdermal absorbability of etodolac is reduced to about one third when the alcoholic composition is increased to the ratio of 4:1. As to the combination of the alcohols and the esters, any alcohol may be used with any ester described above, and examples of a preferable combination include propylene glycol or ethylene glycol as an alcohol, and diethyl sebacate or isopropyl myristate as an ester. The combination of propylene glycol as an alcohol and diethyl sebacate as an ester is more preferable.

"Softening agent" in the present application means an additive to improve a property of the adhesive mass (adhesive layer) and usually a gelled hydrocarbon is used. Further, a petroleum softening agent such as liquid paraffin, vaseline, process oil, or low molecular polybutene; a fatty oil softening agent such as caster oil or palm oil; or purified lanolin may be used for any purpose. In the present invention, a gelled hydrocarbon alone or a combination of one or more sort of softening agents may be used as the softening agent. Preferably, examples of the softening agent added to a gelled hydrocarbon include a petroleum softening agent such as liquid paraffin, vaseline, process oil or low molecular polybutene. More preferably, liquid paraffin or Vaseline is exemplified. Plastibase (trade name) can also be used as a gelled hydrocarbon.

"Tackifier resin" in the present application means any resin applicable to a tape preparation and examples of the same resin include a terpene resin, a polyolefin resin, aromatic petroleum resin, a hydrogenated petroleum resin, rosin and rosin derivative (e.g., hydrogenated rosin). Preferably, a terpene resin (e.g., Clearon p-125, YS resin PX-1150N etc.), a polyolefin resin (e.g., polybutene) and a hydrogenated petroleum resin (e.g., alcon P-100) are exemplified. Among them, the terpene resin is especially preferable. A terpene resin has better thermostability compared to other tackifier resin in a formulation, and an adhesive layer made of a terpene resin is hard to penetrate through a backing cloth. As a result, adhesion of a tape preparation made of the terpene resin is not easily deteriorated and these tackifier resins may be used alone or in combination of two or more thereof for any purpose.

In general a tape preparation is composed of an elastomer and a tackifier, a softening agent, a bulking agent, an antioxidant and the like, and any common and widely-used components may be used in the present invention, especially the bulking agent and the antioxidant may be optionally added or canceled.

Examples of the elastmer above include styrene-isoprene-styrene block copolymer (SIS), styrene-butadiene-styrene block copolymer, styrene-ethylene-butadiene rubber-styrene block copolymer, styrene-butadiene rubber, a synthetic rubber such as polyisoprene, polyisobutylene, polybutene, butyl rubber and silicon rubber etc.; an acrylate resin such as methyl polyacrylate and methyl polymetacrylate; natural rubber and the like. Preferable examples include styrene-isoprene-styrene block copolymer, styrene-butadiene rubber and rubber polymers such as polybutene, polyisoprene, butyl rubber and natural rubber etc. and these may be used alone or in laminated manner of two or more thereof.

Examples of the bulking agent above include zinc oxide, titan oxide, calcium carbonate, silicic acid and the like.

Examples of the antioxidant above include dibutylhydroxytoluene (BHT), 4,4-dioxydiphenyl, EDTA-2Na and the like.

According to a target disease or need, a variable amount of the active ingredient, etodolac, may be included in the present invention. In general, examples of the content of etodolac include 1 to 10 (w/w) %. Preferably 1 to 5 (w/w) % of etodolac is included. More preferably, 2 to 3 (w/w) % of etodolac is included.

A plaster of the present invention including an ionic liquid of etodolac may be prepared according to any method already known and for example it may be prepared by dissolving an ionic liquid of etodolac in a solvent such as toluene, hexane or ethyl acetate etc. together with a vehicle such as an alcoholic solvent, an ester solvent, a softening agent or a tackifier etc., removing the solvent by drying after stretching it on a peeling liner or a backing and finally covering it with another peeling liner or backing.

Any backing may be used in the present invention of a plaster, and for example any stretch backing or non-stretch backing may be used. Examples of the backing include a cloth, a non-woven cloth, polyurethane, polyester, polyvinyl acetate, polyvinylidene chloride, polyethylene, polyethylene terephthalate, aluminium sheet, or a combined material thereof.

A peeling liner used in the present invention of a plaster includes polyester such as polyethylene terephthalate; film such as polyvinyl chloride or polyvinylidene chloride; and laminated film composed of quality paper and polyolefine. In order to provide with a easily removable liner, it is preferable that a surface of liner stuck to the adhesive mass layer is treated with silicon or fluorine.

EXAMPLES

The present invention is more specifically illustrated by the following working examples and test examples but the present invention is never limited to these examples.

Example 1

Formation of an Ionic Liquid of Etodolac by an Organic Amine Compound and Transdermal Absorption An ionic liquid (melt salt) of etodolac is prepared by mixing an equimolar amount of etodolac and an organic amine compound according to a mixing ratio (w/w %) of Table 1 and heated at 80° C. Ingredients other than etodolac were separately dissolved in toluene, the ionic liquid of etodolac was added therein and mixed to give a homogenous solution. A tape preparation was prepared by working a coating machine charged with the said solution. That is, a peeling film (polyester) was coated at first with the solution so that an amount of the adhesive mass is 100 g/m² after being dried and toluene was evaporated by drying under heating. A backing (a non-woven cloth) was attached to a surface of the plaster, the whole film was cut up to give a tape preparation.

Transdermal absorbability of the resulted tape preparation was assayed by using a Franz Cell and the transdermal absorbability of etodolac (μg/cm²) after two hours into the experiment was evaluated. These results were shown in Table 1.

TABLE 1

| | Test No. | | | | |
|---|---|---|---|---|---|
| | Reference Example 1 | 1 | 2 | 3 | 4 |
| Etodolac | 2.4 | 2.4 | 2.4 | 2.4 | 2.4 |
| Organic amine compound | none | lidocaine: 1.96 | TEA: 1.20 | TIA: 1.60 | DIA: 1.10 |
| Organic solvent: | | | | | |
| propylene glycol | 2.0 | 2.0 | 2.0 | 2.0 | 2.0 |
| diethyl sebacate | 2.0 | 2.0 | 2.0 | 2.0 | 2.0 |
| Antioxidant: | | | | | |
| BHT | 1.0 | 1.0 | 1.0 | 1.0 | 1.0 |
| Softening agent | | | | | |
| liquid paraffin | 21.6 | 19.64 | 20.0 | 20.5 | 20.4 |
| white vaseline | 10.0 | 10.0 | 10.0 | 10.0 | 10.0 |
| plastibase | 10.0 | 10.0 | 10.0 | 10.0 | 10.0 |
| Tackifier resin: | | | | | |
| polybutene | 1.0 | 1.0 | 1.0 | 1.0 | 1.0 |
| alcon P-100 | 38.0 | 38.0 | 38.0 | 38.0 | 38.0 |
| Erastmer: | | | | | |
| SIS | 12.0 | 12.0 | 12.0 | 12.0 | 12.0 |
| Total | 100.0 | 100.0 | 100.0 | 100.0 | 100.0 |
| Transdermal absorbability (μg/cm²) | 4.5 | 19.0 | 1.0 | 5.2 | 0.2 |

[Note]
TEA: triethanolamine
TIA: triisopropanolamine
DIA: diisopropanolamine

Transdermal absorbability of a tape preparation including the salt of etodolac (ionic liquid) obtained from etodolac and lidocaine or isopropanolamine was better than that of a tape preparation including etodolac alone. Basicity of the organic amine compounds is shown in Table 2 below and the data suggested that the transdermal absorbability of the etodolac salt is affected by other factors such as hydrophobicity etc. rather than the basicity of the organic amine compounds

TABLE 2

| Acidic substance | pKa | Basic substance | pKa |
|---|---|---|---|
| etodolac | 4.65 | diisopropanolamine | 9.00 |
| | | triisopropanolamine | 8.03 |
| | | lidocaine | 7.86 |
| | | triethanolamine | 7.77 |

The difference of pKa values between etodolac and lidocaine is about 3.2 and an equilibrated mixture was expected but it was confirmed that the mixture of etodolac and lidocaine was not an equilibrated mixture but forms a salt judged from IR and/or H-NMR. The salt-formation was never expected from the difference of pKa values.

As shown in Table 1 above, a lidocaine salt of etodolac had about four times transdermal absorbability compared with that of etodolac without lidocaine. Also, about five times increase was observed in the blood level of etodolac depending on the existence of lidocaine in the in vivo test of rat as illustrated in the test example 2. Accordingly, superior transdermal absorbability was confirmed in the tape preparation including a lidocaine salt of etodolac (an ionic liquid) compared with that of etodolac without lidocaine.

Example 2

Solvent Effect on the Tape Preparation Including an Ionic Liquid of Etodolac (a Salt with Lidocaine)

(1) Solubility of a Lidocaine Salt of Etodolac

Solubility of a lidocaine salt of etodolac (an ionic liquid) in an organic solvent was estimated and an attempt to control of transdermal absorbability was made by adjusting the composition of organic solvent. At first, solubility of a lidocaine salt of etodolac in the organic solvent shown in Table 3 was evaluated.

TABLE 3

| | Conc. of etodolac · lidocaine salt in the solvent | | |
|---|---|---|---|
| Organic solvent | 67% | 50% | 33% |
| propylene glycol | ○ | ○ | ○ |
| 1,3-butanediol | ○ | ○ | ○ |
| glycol salicylate | X | X | ○ |
| glycerin | X | X | X |
| diethyl sebacate | ○ | ○ | ○ |
| isopropyl myristate | Δ | ○ | ○ |
| isopropyl palmitate | Δ | ○ | ○ |
| medium-chain fatty acid triglyceride | Δ | ○ | ○ |
| olive oil | X | X | X |
| liquid paraffin | X | X | X |
| isostearic acid | X | X | X |
| oleic acid | X | X | ○ |

[Note]
○: dissolved
Δ: partially left undissolved
X: not dissolved

Necessity of adding an organic solvent having high solubility to avoid a precipitation of a etodolac salt in the production of the tape preparation was demonstrated since the lidocaine salt of etodolac is hardly soluble in a softening agent such as liquid paraffin etc.

(2) Solvent Effect on Transdermal Absorbability of a Tape Preparation

As shown in Table 3, a lidocaine salt of etodolac had good solubility in alcohols and esters, and solvent effect on transdermal absorbability was investigated as to propylene glycol, 1,3-butanediol and diethyl sebacate selected as a solubilizing agent. At first, tape preparations having the compositions of Table 4 (w/w %) were prepared according to the method of example 1. Then, transdermal absorbability of etodolac (μg/cm²) was evaluated after two hours into the test using Franz Cell according to Test Example 1. The results were also shown in Table 4.

TABLE 4

| | Test No. | | | | | |
|---|---|---|---|---|---|---|
| | Reference Example 2 | 5 | 6 | 7 | 1 | 8 |
| Etodolac | 2.4 | 2.4 | 2.4 | 2.4 | 2.4 | 2.4 |
| Organic amine Compound (lidocaine) | 1.96 | 1.96 | 1.96 | 1.96 | 1.96 | 1.96 |
| Organic solvent: | | | | | | |
| propylene glycol | 0 | 4.0 | | | 2.0 | |
| 1,3-butanediol | 0 | | 4.0 | | | 2.0 |
| diethyl sebacate | 0 | | | 4.0 | 2.0 | 2.0 |
| Antioxidant: | | | | | | |
| BHT | 1.0 | 1.0 | 1.0 | 1.0 | 1.0 | 1.0 |
| Softening agent | | | | | | |
| liquid paraffin | 23.64 | 19.64 | 19.64 | 19.64 | 19.64 | 19.64 |
| white vaseline | 10.0 | 10.0 | 10.0 | 10.0 | 10.0 | 10.0 |
| plastibase | 10.0 | 10.0 | 10.0 | 10.0 | 10.0 | 10.0 |
| Tackifier resin: | | | | | | |
| polybutene | 1.0 | 1.0 | 1.0 | 1.0 | 1.0 | 1.0 |
| alcon P-100 | 38.0 | 38.0 | 38.0 | 38.0 | 38.0 | 38.0 |
| Erastmer: | | | | | | |
| SIS | 12.0 | 12.0 | 12.0 | 12.0 | 12.0 | 12.0 |
| Total | 100.0 | 100.0 | 100.0 | 100.0 | 100.0 | 100.0 |
| Transdermal absorbability ($\mu g/cm^2$) | 9.0 | 8.5 | 8.5 | 7.0 | 19.0 | 18.0 |

As shown in Reference Example 2 and Examples 5-7 of Table 4, transdermal absorbability was not affected so much by the presence or absence of an organic solvent, but about twofold increase of the transdermal absorbability compared with the case using a single solvent was observed when an alcohol and an ester coexist.

Example 3

Composition Change of the Organic Solvent and Effects on the Transdermal Absorbability It was found that coexistence of an alcohol and an ester promotes the transdermal absorbability, and then the best composition of solvents (w/w %) was explored by changing the composition of the alcohol (propylene glycol) and the ester (diethyl sebacate). For the purpose, a tape preparation having the composition of Table 5 (w/w %) below was prepared according to the method of example 1.

Transdermal absorbability of the resulted tape preparation was assayed by using Franz cell and the transdermal absorbability of etodolac ($\mu g/cm^2$) after two hours into the experiment was evaluated. The results were also shown in Table 5.

TABLE 5

| | Test No. | | | | | |
|---|---|---|---|---|---|---|
| | 5 | 9 | 10 | 1 | 11 | 12 |
| Etodolac | 2.4 | 2.4 | 2.4 | 2.4 | 2.4 | 2.4 |
| Organic amine Compound (lidocaine) | 1.96 | 1.96 | 1.96 | 1.96 | 1.96 | 1.96 |
| Organic solvent: | | | | | | |
| propylene glycol | 4.0 | 3.2 | 2.7 | 2.0 | 1.3 | 0.8 |
| diethyl sebacate | | 0.8 | 1.3 | 2.0 | 2.7 | 3.2 |
| Antioxidant: | | | | | | |
| BHT | 1.0 | 1.0 | 1.0 | 1.0 | 1.0 | 1.0 |
| Softening agent | | | | | | |
| liquid paraffin | 19.64 | 19.64 | 19.64 | 19.64 | 19.64 | 19.64 |
| white vaseline | 10.0 | 10.0 | 10.0 | 10.0 | 10.0 | 10.0 |
| plastibase | 10.0 | 10.0 | 10.0 | 10.0 | 10.0 | 10.0 |
| Tackifier resin: | | | | | | |
| polybutene | 1.0 | 1.0 | 1.0 | 1.0 | 1.0 | 1.0 |
| alcon P-100 | 38.0 | 38.0 | 38.0 | 38.0 | 38.0 | 38.0 |
| Erastmer: | | | | | | |
| SIS | 12.0 | 12.0 | 12.0 | 12.0 | 12.0 | 12.0 |
| Total | 100.0 | 100.0 | 100.0 | 100.0 | 100.0 | 100.0 |
| Transdermal absorbability ($\mu g/cm^2$) | 8.5 | 5.8 | 10.3 | 19.0 | 11.0 | 6.3 |

As shown in Table 5, the transdermal absorbability of a lidocaine salt of etodolac was enhanced when the composition ratio of an alcohol (propylene glycol) and an ester (diethyl sebacate) is in a range of 1:2 to 2:1 (w/w %). In addition, the transdermal absorbability of etodolac was reduced to about one third when the alcohol composition was increased and the composition rate of an alcohol (propylene glycol) and an ester (diethyl sebacate) is 4:1 (the Test No. 9).

Example 4

Effect of a Softening Agent on Adhesibility of a Tape Preparation

Adhesibility of a tape preparation is considered to be affected by the amount and types of a softening agent, which is added to an adhesive layer (an elastmer and tackifier). Then, a tape preparation having the composition of Table 6 (w/w %) was prepared according to the method of example 1 in order to study effect of an softening agent on adhesibility of a tape preparation The adhesibility test (Ball-tack test) was carried out for the resulted tape preparations and the result was also shown in Table 6

TABLE 6

|  | Test No. | |
|---|---|---|
|  | 1 | 13 |
| Etodolac | 2.4 | 2.4 |
| Organic amine Compound (lidocaine) | 1.96 | 1.96 |
| Organic solvent: | | |
| propylene glycol | 2.0 | 2.0 |
| diethyl sebacate | 2.0 | 2.0 |
| Antioxidant: | | |
| BHT | 1.0 | 1.0 |
| Softening agent | | |
| liquid paraffin | 19.64 | 39.64 |
| white vaseline | 10.0 | 0 |
| plastibase | 10.0 | 0 |
| Tackifier resin: | | |
| polybutene | 1.0 | 1.0 |
| alcon P-100 | 38.0 | 38.0 |
| Erastmer: | | |
| SIS | 12.0 | 12.0 |
| Total | 100.0 | 100.0 |
| adhesibility test 50° C. 3 M: | | |
| 1 min | No. 8 | No. 7 |
| 30 sec | No. 9 | No. 7 |

[Note]
A steel ball having a diameter of 3.2 mm (No. 1) to 15.9 mm (No. 9) was rolled from the top of a slope and time for sticking on the adhesive surface was measured. No. of the largest diameter which was sticking for the designated period is shown When the Test No. 1 was contrasted with the Test No. 13 in Table 6, the Test No. 1 containing white vaseline and plastibase was more adhesive than the Test No. 13 and shown to have strength enough to be used as a tape preparation.

Also deterioration of adhesibility in the tape preparation the Test No. 1 was improved when preserved under severity condition (at 50° C. for 3 months).

Example 5

Effect of Tackifier

In order to study an effect of tackifier, which is a base of a tape preparation, on the transdermal absorbability of an agent, a tape preparation having the composition of Table 7 (w/w %) was preparaed.

Transdermal absorbability of the resulted tape preparation was assayed by using a Franz cell according to the test example 1 and the transdermal absorbability of etodolac (μg/cm$^2$) after two hours into the experiment was evaluated. The results were also shown in Table 7.

TABLE 7

|  | Test No. | |
|---|---|---|
|  | 1 | 14 |
| Etodolac | 2.4 | 2.4 |
| Organic amine Compound (lidocaine) | 1.96 | 1.96 |
| Organic solvent: | | |
| propylene glycol | 2.0 | 2.0 |
| diethyl sebacate | 2.0 | 2.0 |
| Antioxidant: | | |
| BHT | 1.0 | 1.0 |
| Softening agent | | |
| liquid paraffin | 19.64 | 26.64 |
| white vaseline | 10.0 | 10.0 |
| plastibase | 10.0 | 10.0 |
| Tackifier resin: | | |
| polybutene | 1.0 |  |
| hydrogenated petroleum resin (alcon P-100) | 38.0 |  |
| terpene resin |  | 32.0 |
| Erastmer: | | |
| SIS | 12.0 | 12.0 |
| Total | 100.0 | 100.0 |
| Transdermal absorbability (μg/cm$^2$) | 19.0 | 17.4 |

As shown in Table 7 above, the transdermal absorbability of etodolac was affected little by changing the tackifier.

As illustrated above the similar transdermal absorbability was observed in the evaluation test for the transdermal absorbability in vitro, but the tape preparation of No. 14 gave a preferable blood kinetics of etodolac in the in vivo test (a test of evaluating a blood level) using a hairless rat on the basis of the test example 5, the result of which is shown in FIG. 4.

Since the tape preparation of Test No. 14 had a superior effect, a comparative experiment of the tape preparation of Test No. 14 with other tape preparation (Flector Patch) was carried out using a carrageenan footpad edema model. As a result shown in FIG. 5, No. 14 was shown to be more effective than other tape preparation (Flector Patch).

Test Example 1

Evaluation of Transdermal Absorbability Using Franz Cell

As to each tape preparation prepared on the basis of formulation described in Table 1, transdermal permeability of etodolac in rat in vitro was assayed using Franz Cell.

A receptor chamber of Franz Cell was filled with physiological saline and warmed up to 32° C. Hair of the abdomen of Wister rat (5 weeks-old) was removed the day prior to the test and a piece of the abdominal was picked up. The abdominal skin was applied to the Franz Cell and fixed. Next, each tape preparation is applied on the fixed skin and clipped using a cell cap. One or two hours later, about 300 μl of the test liquid was sampled and analyzed using HPLC (λ: 225 nm).

Test Example 2

Evaluation Test of Blood Level in Rat

Hair is carefully removed from back of the skin in a male SD rat (4 weeks old) using an electric clipper or shaver the day prior to the test. After confirmation that the clipped area is not damaged, the test sample (Test No. 1, Reference Example 1 or Reference Example 3) is applied on the back and occluded by non-woven adhesive dressing. After being occluded for 24 hours, the applied sample is removed and the applied site was wiped with absorbent cotton wetted with warmed water. The applied site is occluded again to prevent the animal from licking it. In addition, reference example 1 and 3 of the second group are applied simultaneously on the same back of one animal avoiding overlap.

The result was shown in FIG. 1. It was found that a tape preparation containing etodolac.lidocaine salt (ionic liquid) gave a blood level 5-times more than that of a tape preparation containing etodolac alone.

Test Example 3

Test of Confirming Structure of Etodolac.Lidocaine Salt (Ionic Liquid)

(1) Preparation of Test Sample
A etodolac.lidocaine salt:
Equimolar of etodolac (2.4 g) and lidocaine (1.96 g) were mixed at about 70° C. and cooled to room temperature to give a highly viscous gelatin-like oily matter.
B a propylene glycol solution of etodolac.lidocaine salt:
Etodolac (2.4 g), lidocaine (1.96 g) and propylene glycol (4.4 g) were mixed at 50° C. to give an oily matter.
(2) Elementary Analysis
As a result of the elementary analysis of etodolac.lidocaine obtained in a above, measured values corresponded with calculated values in Table 8.

TABLE 8

|  | C (%) | H (%) | N (%) |
|---|---|---|---|
| Calculated for $C_{31}H_{41}N_3O_4$ | 71.65 | 7.95 | 8.09 |
| Found | 71.80 | 7.86 | 8.18 |

(3) Measure of IR Spectrum
IR absorption spectrum was measured using Fourier transform IR spectrometer (FTIR-8400S, Shimazu Corporation).

Etodolac lidocaine salt of A above was so viscous that it was dissolved in a small amount of chloroform, sandwiched between NaCl plates and measured. On the other hand, the PG solution of etodolac-lidocaine B was directly measured with being sandwiched between NaCl plates. In addition, each of etodolac and lidocaine was measured for comparison in chloroform and propylene glycol (PG) respectively.

The Result was Shown in Table 9 Below.

TABLE 9

| Compounds | Assignment | wavenumber of C=O stretching vibration ($cm^{-1}$) | |
|---|---|---|---|
|  |  | in chloroform | in PG |
| etodolac | —COOH | 1705 | 1710 |
| lidocaine | —$CONR_2$ | 1670 | 1665 |
| etodolac | —COO— | unclear | 1575 |
| lidocaine | —$CONR_2$ | 1670 | 1675 |

As to IR spectrum of etodolac, a broad absorption band based on C=O stretching vibration of the free carboxylic group was found at 1705 $cm^{-1}$ and 1710 $cm^{-1}$ in chloroform and PG respectively. As to lidocaine, C=O stretching vibration of the amidocarbonyl group was detected as a broad absorption band at 1665 to 1670 $cm^{-1}$.

In the case of etodolac.lidocaine, any peak based on the free —COOH was observed at 1705 to 1710 $cm^{-1}$ neither in chloroform nor PG. In IR spectrum of the PG solution, however, a new absorption band based on the carboxyl anion (COO—) was observed at 1575 $cm^{-1}$.

(4) Measure of Proton NMR Spectrum
Proton NMR spectrum was measured using Fourier transform 400 mHz NMR spectrometer (Ultra Shield 400 Plus, Bruker Inc.).

Each of the etodolac.lidocaine salt of A above, etodolac alone and lidocaine alone was dissolved in chloroform-d3 and NMR spectrum was measured.

The result was shown in Table 10 and 11.

TABLE 10

| a) Assignment of etodolac-moiety | Multiplicity | Relative ratio | Value of Chemical shift ($\delta$, ppm) | | $\Delta\delta$ (A − B) |
|---|---|---|---|---|---|
|  |  |  | (A) | (B) |  |
| 1-$CH_2\underline{CH}_3$ | t | 3 H | 0.84 | 0.88 | −0.04 |
| 8-$CH_2\underline{CH}_3$ | t | 3 H | 1.31 | 1.32 | −0.01 |
| 1-$C\underline{H}_2CH_3$ | m | 2 H | 2.06 | 2.07 | −0.01 |
| 4-$C\underline{H}_2$— & 8-$C\underline{H}_2CH_3$ | m | 4 H | 2.8 | 2.8 | 0 |
| 1-$C\underline{H}_2COO$ | dd | 2 H | 2.95 | 3.05 | −0.10 |
| 2-$C\underline{H}_2$—O— | m | 2 H | 4.08 | 4.08 | 0 |
| H on the benzene ring | m | 3 H | 7.0-7.4 | 7.0-7.4 | 0 |

(A): etodolac-lidocaine
(B): etodolac

TABLE 11

| a) Assignment of lidocaine-moiety | Multiplicity | Proton number | Value of Chemical shift ($\delta$, ppm) | | $\Delta\delta$ (A − C) |
|---|---|---|---|---|---|
|  |  |  | (A) | (C) |  |
| N—$(CH_2\underline{CH}_3)_2$ | t | 6 H | 1.17 | 1.14 | +0.03 |
| Aromatic $\underline{CH}_3$ | s | 3 H | 2.22 | 2.23 | −0.01 |
| N—$(\underline{CH}_2CH_3)_2$ | q | 4 H | 2.80 | 2.69 | +0.11 |
| N—$\underline{CH}_2CONH$— | s | 2 H | 3.36 | 3.22 | +0.14 |
| $\underline{H}$ on the benzene ring | m | 3 H | 7.1 | 7.1 | 0 |
| —CON$\underline{H}$— | b-s | 1 H | 9.2 | 8.9 | +0.3 |

(A): etodolac-lidocaine
(C): lidocaine

Measurement of IR and NMR spectrums supported that etodolac and lidocaine are not a mixture of both compounds but form a salt to be a new ionic liquid compound between etodolac and lidocaine.

Reference Example 3

Preparation of a Tape Preparation Comprising Lidocaine Alone

Lidocaine 0.98 g, propylene glycol 1.0 g, diethyl sebacate 1.0 g, BHT 0.5 g, liquid paraffin 10.08 g, white petrolatum 5.0 g, plastibase 5.0 g, polybutene 0.5 g, alcon P-100 19.0 g and SIS 6.0 g were dissolved in toluene and a tape preparation was prepared by working a coating machine according to example 1.

Reference Example 4

Preparation of a Tape Preparation Comprising a Base Alone without Etodolac and Lidocaine Propylene glycol 2.0 g, diethyl sebacate 2.0 g, BHT 1.0 g, liquid paraffin 19.64 g, white petrolatum 10.0 g, plastibase 10.0 g, polybutene 1.0 g, alcon p-100 38.0 g and SIS 12.0 g were dissolved in toluene and a tape preparation was prepared by working a coating machine according to example 1.

Test Example 4

Test for Confirming Anti-Inflammatory or Analgesic Effect of a Tape Preparation Comprising Etodolac.lidocaine Salt (ionic liquid)

(1) Evaluation Test of a Tape Preparation with a Rat Model of Adjuvant Arthritis A male SPF rat (seven weeks old) was used. Measurement was carried out with a footpad volume measuring apparatus (Unicorn). A tuberculin syringe (1 ml) is filled with a suspension of liquid paraffin containing 6 mg/ml of Mycobacterium B. (hereinafter called adjuvant) and 0.05 ml/rat is transdermally administered at the bottom tail. In addition, hair around the injection site is shaved before the transdermal administration with an electrical hair clipper.

On the $14^{th}$ day after administration of adjuvant, footpad volumes of right and left legs are measured and a rate of footpad edema in each leg and a total of the rate in both legs are calculated on the basis of footpad volume before the administration of adjuvant.

Each tape preparation (2.5×2.5 cm) of a sample substance (tape preparations of the test example 1, or the reference example 4, Flector Tape or Mohrus Tape) was applied so as to cover whole right and left legs once a day for 5 days. For 6 hours after the application, the applied tape preparation was covered to prevent the animal from licking the preparation.

The result was shown in FIG. 2. An anti-inflammatory effect was observed in the tape preparation of test example 1 as well as Flector Tape or Mohrus Tape.

(2) Evaluation Test of a Tape Preparation with a Rat Pain Model of Beer Yeast-Induced Inflammation A pain threshold in the footpad of the right leg is measured in a male SD rat (five weeks old) using a measure apparatus of analgesic effect against pressure stimulation (Ugo Basile). Rats are divided into groups on the basis of the pain threshold. On the next day after being divided, each of tape preparation of a sample substance (tape preparation of the test example 1, or the reference example 4, Flector Tape or Mohrus Tape) is applied to a rat so as to cover the footpad and moreover fixed with a surgical tape etc. A rat of non-treated group was only fixed with a surgical tape.

After a lapse of a certain period of time since a test sample was applied, 1 ml of a 10% physiological saline solution of beer yeast was transdermally administered to the footpad of right leg. Each of 0.5, 1, 2 and 3 hours after the injection of beer yeast, a pain threshold of the right leg was measured in the same manner and rate of the pain thresholds was calculated.

The result is shown in FIG. 3. It was shown that the tape preparation of test example 1 had the same anti-inflammatory effect as that of Flector Tape or Mohrus Tape.

Test example 5

Evaluation Test for the Blood Level in a Hairless Rat

As to a male hairless rat (6 weeks old), it was confirmed that there is not any damage such as a wound at an application site on the back skin. Test sample (Test No. 1, No. 14 or Reference Example 1) is applied to the back of a rat in each group and occluded by being swaddled with a non-woven adhesive dressing. After being occluded for 48 hours, the applied sample is removed and the applied site is wiped with absorbent cotton wetted with warmed water. The applied site is occluded again to prevent the animal from licking it. A blood sample was collected from the tail vein of a rat and the blood level of etodolac was evaluated by LC/MS/MS The result is shown in FIG. 4. It was shown that Test No. 14 gave the favorable blood level than Test No. 1.

Test Example 6

Anti-Inflammatory Effect of a Tape Preparation of Etodolac.Lidocaine Salt (Ionic Liquid)

(1) Evaluation Test of a Tape Preparation with a Rat Model of Carrageenin-Induced Footpad Edema Footpad volume of the right leg in male SD rat (5 weeks old) is measured using a footpad volume measuring apparatus (Unicorn). Animals are divided into groups according to the resulted footpad volume as an index. The footpad volume of the right leg is measured after fasting of ca 18 hours from the date dividing into groups.

Test sample (Test No. 14 or Flector) is administrated by applying the tape preparation (2.5×2.5 $cm^2$) so as to cover whole right leg and the preparation was further fixed with a surgical tape. In addition, a rat was covered with a hood to prevent the animal from licking it during the period from the application of the test sample to complete administration of the proinflammatory agent.

After a lapse of a certain period of time since a test sample was applied, 0.1 ml of a 1% physiological saline solution of carrageenin was transdermally administered into footpad of right leg. Each of 3, 4 and 5 hours after the injection of carrageenin a volume of the right leg footpad was measured and rate of the edema was calcurated based on the volume of footpad.

The result was shown in FIG. 5. It was shown that the tape preparation of Test No. 14 has superior anti-inflammatory effect than that of Flector.

Test Example 7

Tissue Penetratability of Tape Preparation of Etodola.Lidocaine Salt (Ionic Liquid)

(1) Muscle Tissue of Right Leg in a Rat

In order to evaluate the drug-penetratability of Test No. 14 in vivo, a method using the leg of a rat was considered. Drug-penetratability into a deep part of muscle tissue was evaluated by measuring sample concentration in muscle of the leg in a rat. Fector (diclofenac Epolamine 1.3%) was used as a positive control.

Four male SD rats (5 weeks old) with the leg sheared the day before the test day were used as a group. Test samples (Test No. 14 and Flector) were applied with a size of 2.5×2.5 cm. The applied site is covered with a gauze and occluded by being swaddled with an adhesive dressing. After a lapse of a certain period of time since a test sample was applied, an animal is killed by blood removal under anesthesia. Later the leg was amputated, divided into skin and other tissues and the drug concentration in the muscle tissue was assayed.

The time-shift of the drug-concentration in the resultant tissue was shown in FIG. 6. AUC (0-24)s of the tissue concentration calculated from the result were 235 μg/ghr and 141 μg/ghr with respect to Test No. 14 and Flector respectively. It was shown that the tape preparation of Test No. 14 has about 1.7-fold efficacy compared with AUC of Flector.

(2) Muscle Tissue of the Abdomen in a Rat

The drug-penetratability into muscle tissue of the abdomen in a rat was evaluated in the same manner as (1) above.

Four male SD rats (5 weeks old) with the abdomen sheared the day before the test day was used as a group. Test samples (Test No. 14 and Flector) were applied with a size of 3×4 cm. The applied site is covered with a gauze and occluded by being swaddled with an adhesive dressing. After a lapse of a certain period of time since a test sample was applied, an animal is killed by blood removal under anesthesia. Later the abdomen was cut, and a part of skin at the applied site was picked up. The collected part of skin was divided into skin and other tissues and the drug concentration in the muscle tissue was assayed.

The time-shift of the drug-concentration in the resultant tissue was shown in FIG. 7. AUC (0-24)s of the tissue concentration calculated from the result were 44 μg/ghr and 24 μg/ghr with respect to Test No. 14 and Flector respectively. It was shown that the tape preparation of Test No. 14 has about 1.8-fold efficacy compared with AUC of Flector.

Test Example 8

Change of the Tissue Concentration on the Basis of The Difference of Administration Route of Etodolac The tissue concentrations of etodolac penetrated into muscle tissue in the leg of a rat were compared with between oral and transdermal administrations, and thus the efficacy of the tape preparation of the present invention is demonstrated.

In the case of oral administration, four male SD rats (5 weeks old) are used as a group and 12 mg/kg of etodolac suspended in CMC is forced to be taken in by using a probe. The dose is fixed around about 1.1~1.5 mg/rat. After a lapse of a certain period of time since the forced feeding, an animal is killed by blood removal under anesthesia. Later the leg was amputated, divided into skin and other tissues and the drug concentrations in the muscle tissue and plasma were assayed.

In the case of transdermal administration, sample of Test No. 14 was applied to the leg with a tape having an area of 6.25 cm$^2$ in the same manner as Test example 6(1). The applied area of the sample was adjusted so that transdermally available amount of etodolac was about 0.7 mg/rat when applied for 24 hours. After a lapse of a certain period of time since the application of the sample, an animal is killed by blood removal under anesthesia. Later the leg was amputated, divided into skin and other tissues and the drug concentrations in the muscle tissue and plasma were assayed.

The time-shift of the drug-concentration in the resultant muscle tissue was shown in FIG. 8. It was found that the drug-concentration in the muscle tissue was remarkably increased when transdemally administrated though it was not increased so much when orally administrated. Also AUC (0-24)s calculated from the time-shift of the drug-concentration in plasma and muscle tissue are shown in FIG. 9. In the case of transdemal administration of Test No. 14, when an effective dose of etodolac per one rat was adjusted almost the same, it was demonstrated that the drug-permeability when Test No. 14 was transdermally administrated was about 6 fold higher than the penetratability when etodolac was orally administrated.

Test Example 9

Parallel Comparison Test of Transdermal Absorbability Between the Preparation of the Present Invention (Test Example No. 1) and a Preparation of Patent Literature 2 (JP2005-239709A)

In order to demonstrate usefulness of the preparation of the present invention, a parallel comparison test between the preparation of the present invention and a tape preparation of etodolac described in Patent literature 2 was considered. Then, a tape preparation of Test Example No. 1 with the composition of Table 12 (w/w %) and a tape preparation of Production Example 2 in Patent literature 2 were prepared, and evaluating test of transdermal absorbability was carried out using Franz cell according to Test example 1. Each sample was applied to abdominal skin of a rat and transdermal absorbability (μg/cm$^2$) of etodolac after 6 hours was measured. The result was shown in Table 12.

TABLE 12

| | Test No. | |
|---|---|---|
| | Patent literature 2 (Production example 2) | 1 |
| etodolac | 5.0 | 2.4 |
| Organic amine compound (lidocaine) | 4.0 | 1.96 |
| Organic solvent: | | |
| propylene glycol | | 2.0 |
| diethyl sebacate | 2.0 | 2.0 |
| polyethylene glycol | 7.0 | |
| Antioxidant: BHT | 1.0 | 1.0 |
| Softening agent: | | |
| liquid paraffin | 20.0 | 19.64 |
| white vaseline | | 10.0 |
| plastibase | | 10.0 |
| glycerin | 35.0 | |
| Tackyfier: | | |
| polybutene | 2.0 | 1.0 |
| hydrogenated petroleum resin (alcon p-100) | 16.0 | 38.0 |
| Elastmer: | | |
| SIS | 8.0 | 12.0 |
| Total | 100.0 | 100.0 |
| Transdermal absorbability(μg/cm$^2$) | 25 | 93 |

As shown in Table 12, it was demonstrated that the preparation of the present invention (Test Example No. 1) had about 4-fold of transdermal absorbability of etodolac than that of the tape preparation disclosed in Production Example 2 of Patent literature 2 even though the concentration of contained etodolac was about one half.

One of the reasons why the transdermal absorbability is quite different was attributed to the fact that the composition rate between diethyl sebacate and polyethylene glycole was 1:3.5 and far from the preferable range in the present invention (1:2 to 2:1), in other words content of polyethylene glycol was too much.

INDUSTRIAL APPLICABILITY

Figure 1:
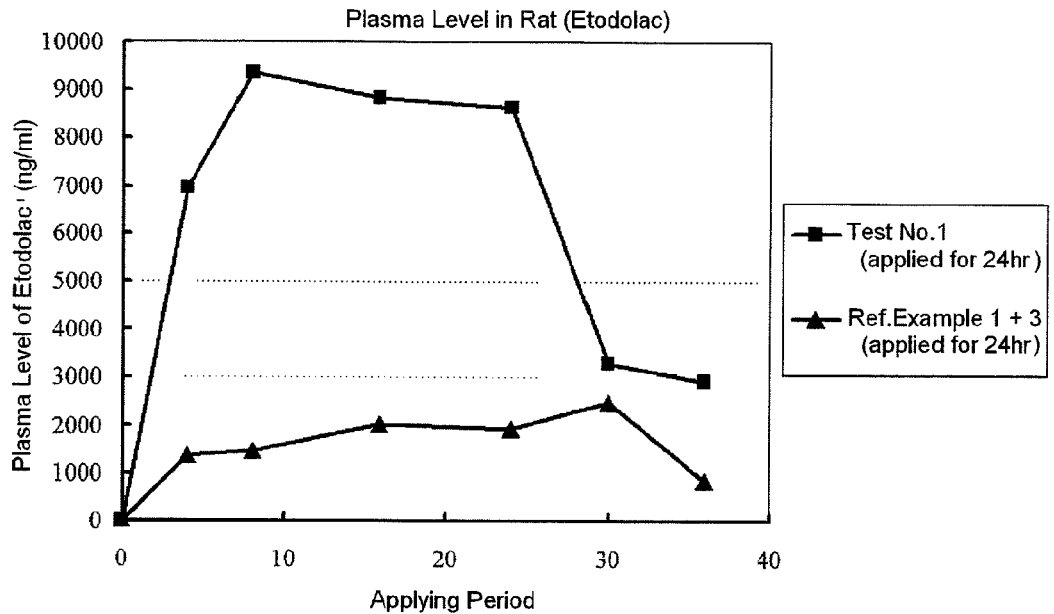
FIG. 1 is a graph showing a time-shift of the concentration of etodolac in plasma for 24 hours.
Figure 2:
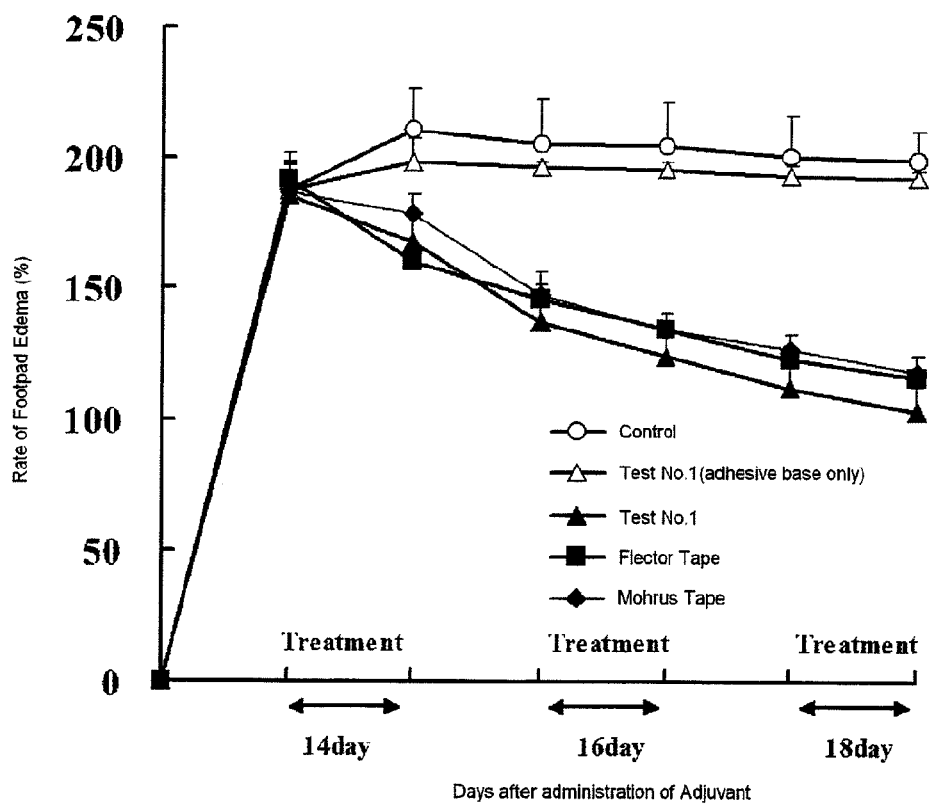
FIG. 2 is a graph showing an effect of the tape preparation in a rat model of adjuvant arthritis.
Figure 3:
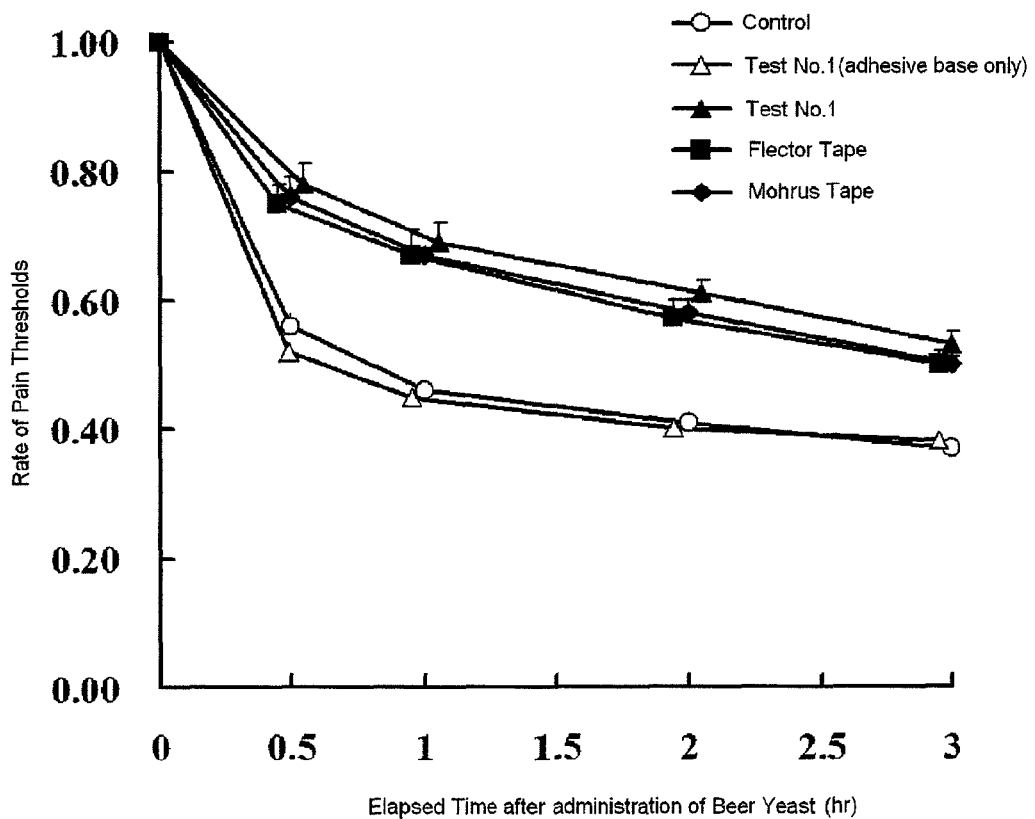
FIG. 3 is a graph showing an effect of the tape preparation in a rat pain model of beer yeast-induced inflammation.
Figure 4:
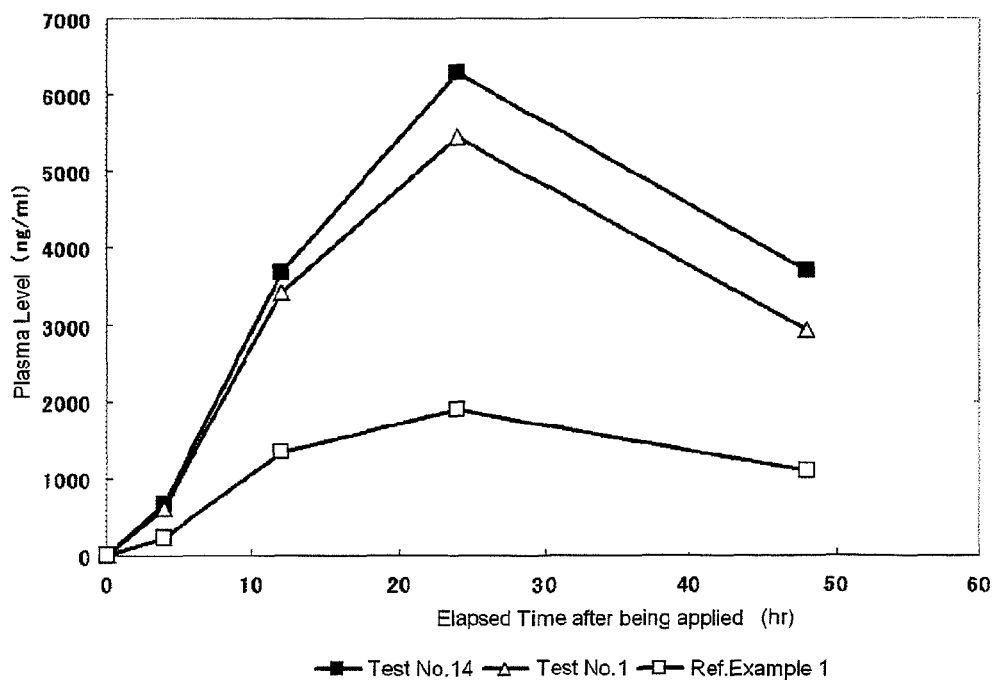
FIG. 4 is a graph showing a change of the concentration in blood when a tape preparation was applied to a hairless rat.
Figure 5:
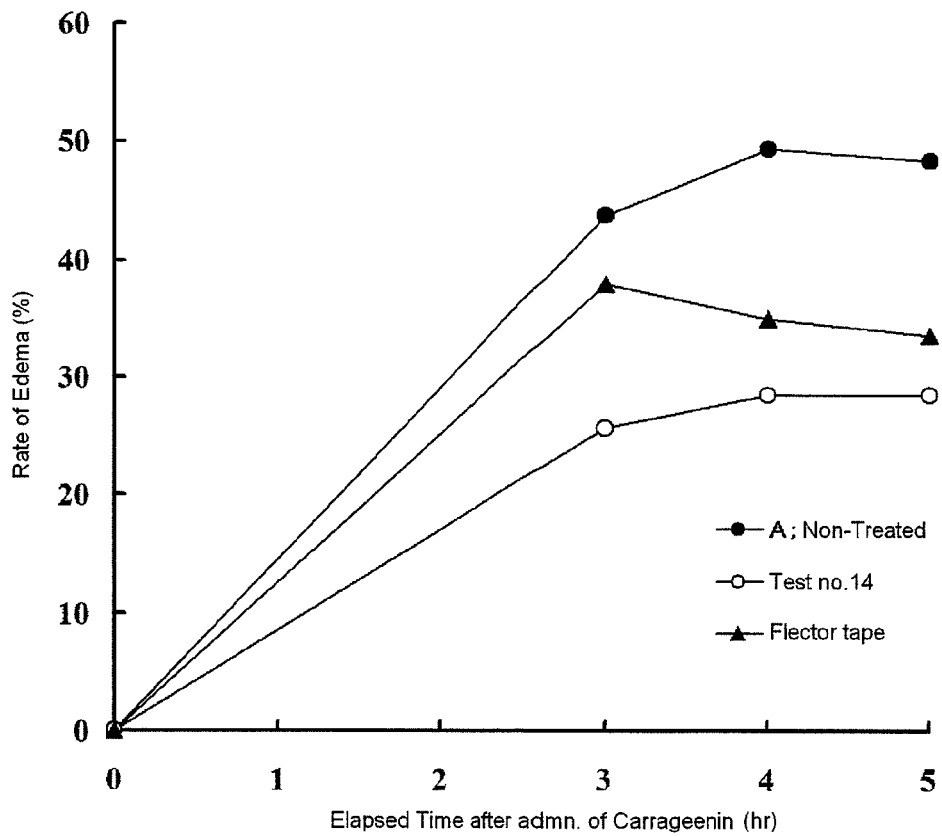
FIG. 5 is a graph showing an effect of the tape preparation in a rat model of carrageenin-induced footpad edema.
Figure 6:
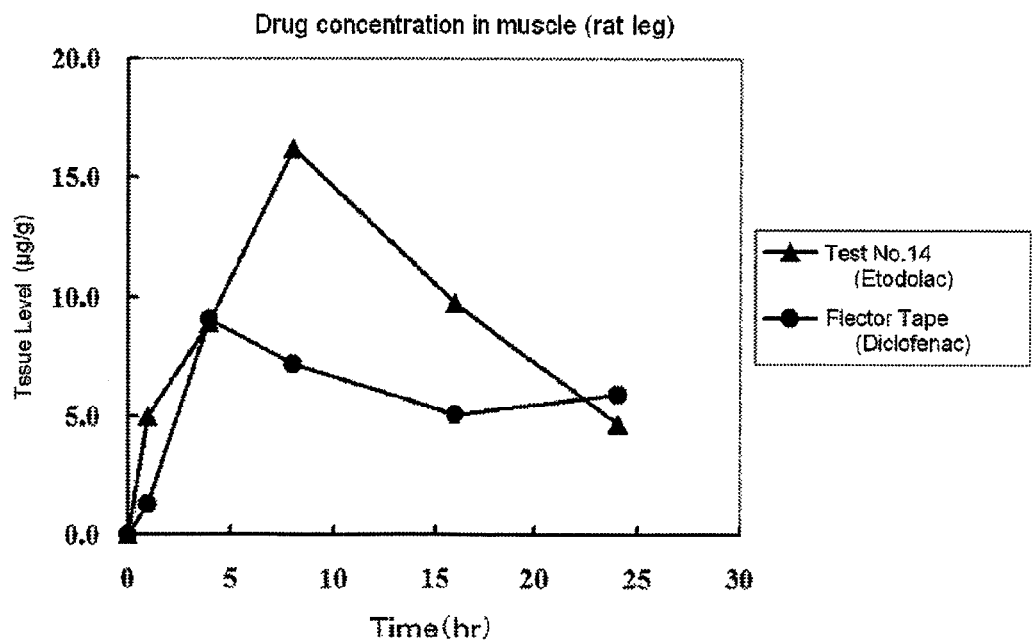
FIG. 6 is a graph showing a shift of the drug-concentration in muscle tissue of the leg in a rat after application of a tape preparation.
Figure 7:
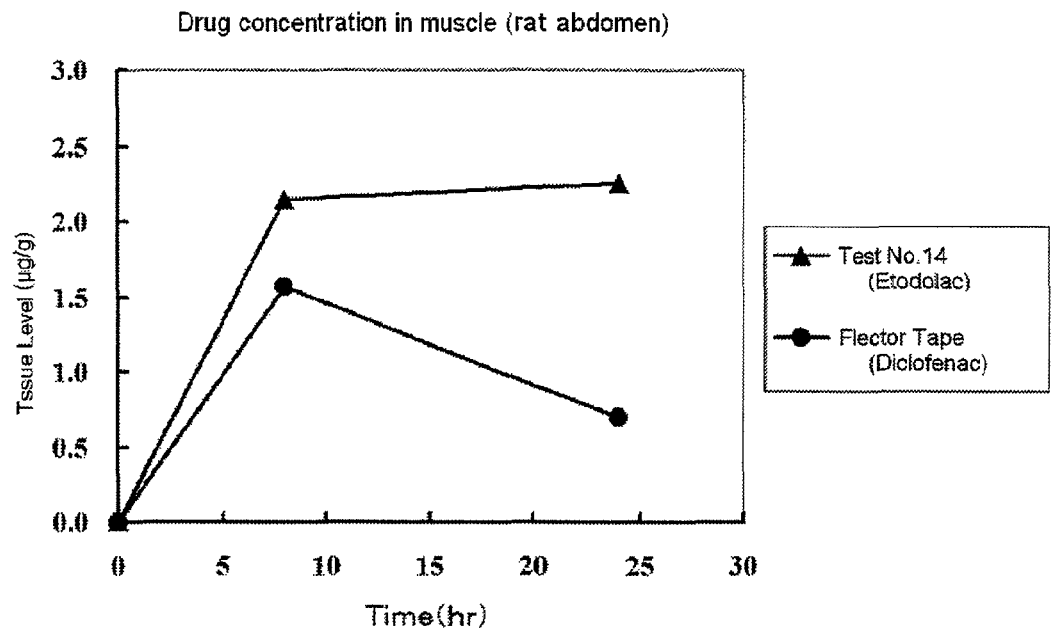
FIG. 7 is a graph showing a shift of the drug-concentration in abdominal muscle tissue in a rat after application of a tape preparation.
Figure 8:
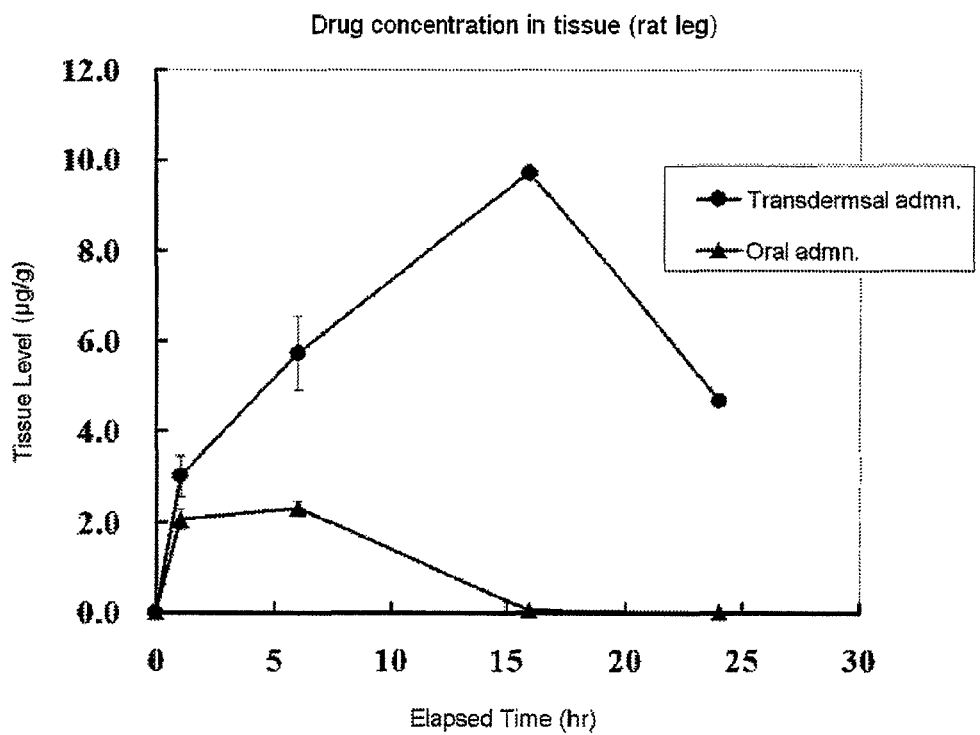
FIG. 8 is a graph showing a time-shift of the drug-concentration in muscle tissue, in which a difference between oral and transdermal administration of etodolac is reflected.
Figure 9:
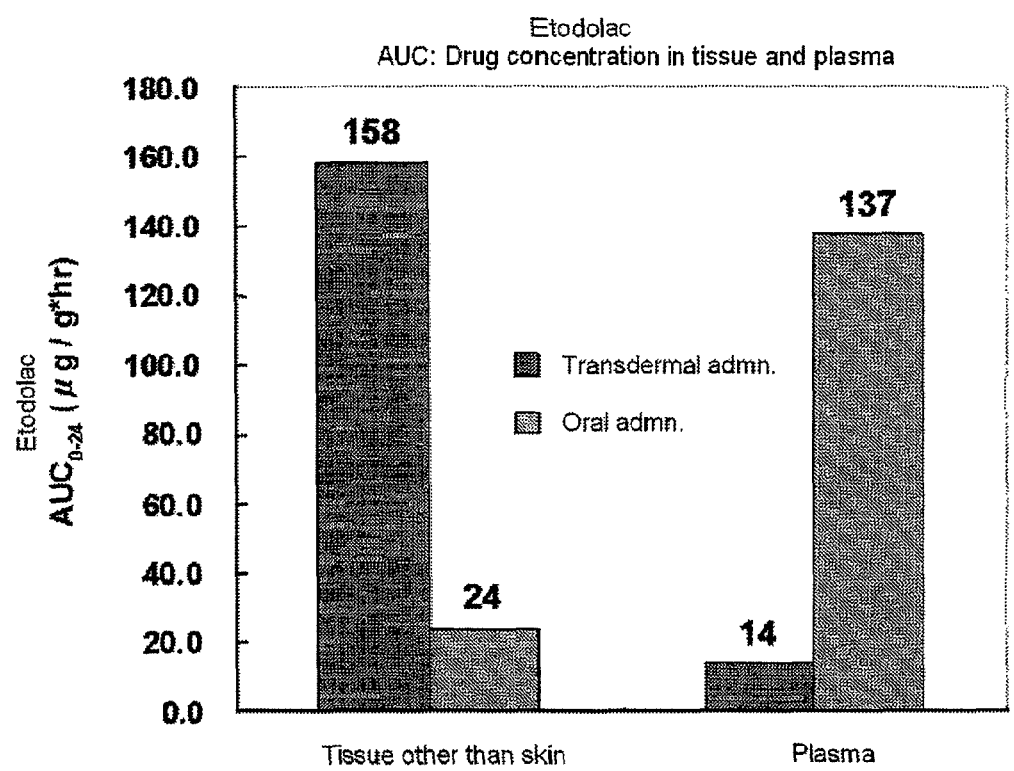
FIG. 9 is a graph showing AUC of the drug-concentration in muscle tissue and plasma, in which a difference between oral and transdermal administration of etodolac is reflected.

An etodolac tape preparation of the present invention has an excellent transdermal absorbability, tissue permeability and suitable adhesivility by means of an ionic liquid of etodolac and several improvement of component. As a result, tissue permeability of etodolac into an affected site having a pain is accelerated, and it became possible to provide with a DDS formulation useful for treating chronic pain such as chronic rheumatoid arthritis, osteoarthritis or low back pain etc., inflammatory diseases such as shoulder periarthritis or thecitis etc., cervico-omo-brachial syndrome, pain of operation or trauma etc.

The invention claimed is:

1. A tape preparation, comprising:
    a) an ionic liquid of etodolac, wherein the etodolac forms an equimolar salt with lidocaine,
    b) an organic solvent, comprising an alcohol and diethyl sebacate which are mixed in a ratio of 1:2 to 2:1 (w/w %), wherein the alcohol is propylene glycol or 1,3-butanediol,
    (c) plasticized hydrocarbon gel, petrolatum and a liquid paraffin as a softener, and
    d) styrene-isoprene-styrene block copolymer as an elastomer.

2. The tape preparation according to claim 1, which comprises 1 to 5 (w/w) % of etodolac.

3. The tape preparation according to claim 1, wherein the alcohol and diethyl sebacate are added in a ratio of 1:1 (w/w %).

4. The tape preparation according to claim 2, wherein the alcohol and diethyl sebacate are added in a ratio of 1:1 (w/w %).

5. The tape preparation according to claim 3, which further comprises at least one tackifier resin selected from the group consisting of polybutene, a hydrogenated petroleum resin, and a terpene resin.

6. The tape preparation according to claim 5, wherein the tackifier resin is a terpene resin.

7. The tape preparation according to claim 1, wherein the petrolatum is white petroleum.

8. The tape preparation according to claim 1, wherein the white petrolatum and the plasticized hydrocarbon gel are present in a ratio of 1:1 (w/w %).

* * * * *